United States Patent [19]
Oliver

[11] Patent Number: 5,961,700
[45] Date of Patent: Oct. 5, 1999

[54] FILTER SYSTEM FOR REMOVAL OF GAS AND PARTICULATES FROM CELLULAR FLUIDS

[75] Inventor: Dana A. Oliver, East Weymouth, Mass.

[73] Assignee: SIMS Level 1, Rockland, Mass.

[21] Appl. No.: 08/962,596

[22] Filed: Oct. 31, 1997

[51] Int. Cl.⁶ ............................................. B01D 19/00
[52] U.S. Cl. .......................... 96/158; 55/337; 55/421; 96/167; 96/171; 96/177; 96/209; 210/188
[58] Field of Search ............................ 95/241, 254, 261; 96/155, 158, 165, 167, 177, 188, 189, 190, 168, 171, 145, 204, 208, 209, 216; 210/188; 55/337, 421

[56] References Cited

U.S. PATENT DOCUMENTS

| | | |
|---|---|---|
| 2,784,733 | 3/1957 | Martinez . |
| 2,879,784 | 3/1959 | Cutter .................................... 137/192 |
| 3,105,511 | 10/1963 | Murphy .................................. 137/399 |
| 3,276,188 | 10/1966 | Carlson .................................... 96/212 |
| 3,476,251 | 11/1969 | Kudlaty .................................. 210/436 |
| 3,512,940 | 5/1970 | Shapiro . |
| 3,616,802 | 11/1971 | Marinaccio .............................. 55/417 |
| 3,771,290 | 11/1973 | Stethem ............................... 210/512.1 |
| 3,834,126 | 9/1974 | Diminno, Jr. ............................ 55/327 |
| 3,993,062 | 11/1976 | Jess .................................... 128/214 R |
| 4,004,587 | 1/1977 | Jess .................................... 128/214 R |
| 4,013,072 | 3/1977 | Jess .................................... 128/214 R |
| 4,028,254 | 6/1977 | Shufflebarger et al. .................. 55/498 |
| 4,102,655 | 7/1978 | Jeffrey et al. ............................ 96/204 |
| 4,345,919 | 8/1982 | Wilkinson et al. ...................... 95/261 |
| 4,365,980 | 12/1982 | Culbert et al. ........................... 55/498 |
| 4,368,118 | 1/1983 | Siposs ..................................... 96/208 |
| 4,411,783 | 10/1983 | Dickens et al. ......................... 210/304 |
| 4,448,206 | 5/1984 | Martell ................................... 128/765 |
| 4,492,634 | 1/1985 | Villa-Real .............................. 210/398 |
| 4,572,724 | 2/1986 | Rosenberg et al. .................... 210/436 |
| 4,601,712 | 7/1986 | Cole et al. .............................. 604/251 |
| 4,662,906 | 5/1987 | Matkovich et al. ..................... 55/318 |
| 4,690,762 | 9/1987 | Katsura ................................. 210/436 |
| 4,758,337 | 7/1988 | Kohn et al. ............................. 96/219 |
| 4,761,232 | 8/1988 | Bright ............................... 210/500.36 |
| 4,806,135 | 2/1989 | Siposs ..................................... 55/204 |
| 4,870,987 | 10/1989 | Cheng .................................... 137/192 |
| 4,900,308 | 2/1990 | Verkaart ................................ 604/126 |
| 4,919,802 | 4/1990 | Katsura ................................. 210/188 |
| 4,932,987 | 6/1990 | Molina .................................... 55/487 |
| 4,964,984 | 10/1990 | Reeder et al. ......................... 210/188 |
| 5,045,096 | 9/1991 | Quang et al. ............................ 96/155 |
| 5,224,515 | 7/1993 | Foster et al. ............................ 138/89 |
| 5,429,595 | 7/1995 | Wright, Jr. et al. .................... 210/188 |
| 5,484,474 | 1/1996 | Weinstein et al. ....................... 55/337 |
| 5,514,095 | 5/1996 | Brightbill et al. ..................... 604/113 |
| 5,707,431 | 1/1998 | Verkaart ................................. 96/177 |

FOREIGN PATENT DOCUMENTS 3837 896  5/1990  Germany .

Primary Examiner—Duane S. Smith
Attorney, Agent, or Firm—Dickinson Wright PLLC

[57] ABSTRACT

A gas elimination system includes a gas elimination device and a priming system. The gas elimination device includes a vortex chamber that forms a vortex in the fluid flowing into the chamber and a particulate filter that removes particles from the fluid. The particulate filter is located in the vortex chamber such that the vortex is formed in a substantial volume of the chamber before it encounters the particulate filter. When the fluid encounters the particulate filter, the vortex is generally stopped, and additional released gasses rise through the open top of the particulate filter. The device also includes an outlet chamber connected to the vortex chamber, and the particulate filter extends into the outlet chamber. A check valve is located at the outlet of the outlet chamber to shut off flow when the device contains excess gas. The priming system in the form of a pillow block is arranged to force air or fluid upward to dislodge the check valve, should it become stuck in the valve seat.

13 Claims, 2 Drawing Sheets

FILTER SYSTEM FOR REMOVAL OF GAS AND PARTICULATES FROM CELLULAR FLUIDS

TECHNICAL FIELD

This invention relates to the art of filters for removing gas and particulates from fluids, particularly cellular fluids. The invention finds particular utility in the removal of air and particulates from blood during transfusions.

BACKGROUND ART

It is often necessary to remove unwanted particles and gasses from fluids by filtering. An example of this is in the infusion of physiological fluids, including blood and blood products. The removal of gasses is even more important when the fluids have been warmed, because of the outgassing caused by the warming.

Because the particles, gasses, and fluid have different densities, it is known to separate these by centrifugal forces arising in a vortex generated in the fluid. Thus, it is known to provide the fluids to a separation chamber by way of an inlet that is tangential to the chamber. The entering fluids are directed into a circular flow pattern, and the gasses tend to accumulate in the center of the chamber while the heavier particles and fluids go to the outside of the chamber. The gasses are allowed to exit the chamber through a vent, and the particles are removed from the fluid by a physical filter.

These devices have faced several problems, particularly when used with cellular fluids. One problem has been the formation of a vortex large enough to remove substantial amounts of gas. The physical arrangement of the various elements of prior devices has constricted the vortex, preventing effective removal of gas. Further, prior art devices have not generally allowed the operator to view operation of the vortex, thus precluding easy verification of proper operation of the device.

Another problem has been clogging due to build up of particulates and cellular globules in the filter medium. This buildup can effectively block the passage of gasses and prevent their separation from the fluid.

A further feature employed in this type of device is that of a check valve. A check valve is placed in the outlet line for stopping further flow through the device when it becomes full of removed air. This occurs, for example, when the amount of air in the fluid exceeds the ability of the device to remove it. Because of the danger of infusing air, or other gasses, into the patient, a check valve that senses the presence of excess air must be placed in the outlet line to block flow of the gasses to the patient. In some instances, these check valves are separate from the filter, which complicates manufacture, inventory, and assembly. Further, prior art check valves often become stuck in the closed position or inhibit fluid flow when open by entrainment of the valve in the fluid flow.

It is an object of this invention to overcome these and other defects by a filter that is compact, easily manufactured, and efficient.

SUMMARY OF THE INVENTION

In accordance with the invention, a filter is provided that is capable of removing large amounts of gas, including air, from fluids such as physiological fluids. In overall design, the filter includes a vortex chamber for removal of gasses and an outlet chamber containing a check valve. The vortex and outlet chambers are axially aligned, the outlet chamber being below the vortex chamber. The vortex chamber is preferably cylindrical, but may be of other rotational shapes that will support the swirling flow of a vortex. For example, the vortex chamber may be conical. The vortex chamber has an inlet in the upper part of the vortex chamber for admitting fluids to be filtered to the vortex chamber. The vortex chamber includes a fluid outlet for the filtered fluids in the lower part of the chamber and a gas outlet in the upper part of the chamber for discharging gasses removed from the fluids to the atmosphere. The inlet is directional and is oriented such that the entering fluids flow in a direction that is tangent to the side of the chamber, whereby a vortex is formed as the fluids flow into the chamber. The fluids and particulates are thrown to the outside of the chamber by this vortex, and the gasses accumulate in the center of the vortex chamber.

The removed gasses rise to the top of the vortex chamber and exit to the atmosphere through a hydrophobic membrane that covers the top of the chamber. This membrane is mounted on a solid first part onto which is snapped a flexible cover. The flexible cover has a gas outlet opening that seals against the solid part when the pressure in the container is less than atmospheric and is lifted to release excess gas when the pressure is larger than atmospheric.

The fluids and particulates flow downward and pass to the outlet chamber through a particulate filter that removes particulates from the fluid. This particulate filter is elongate and coaxial with the vortex and outlet chambers and is positioned to extend upward into the vortex chamber and downward into the outlet chamber. The top of the particulate filter is spaced vertically below the inlet by a distance large enough to allow formation of a substantial vortex flow. This construction provides increased filter area and allows the operator to view the functioning of the vortex.

The top of the particulate filter is open to allow gasses separated from the fluids after passing through the particulate filter to rise to the top of the vortex chamber. Thus, the diameter of the vortex chamber is such that in this part of the filter, the upward velocity of the released gas is greater than the downward velocity of the fluid to allow further gas separation. The fluid can flow into the filter through both the open top and the sides of the particulate filter medium. Thus, some of the particulates are removed from the fluid during flow through the sides of the filter medium in the vortex chamber. As the fluid flows into the outlet chamber, it passes through that portion of the particulate filter that extends into the outlet chamber and is filtered further. A fluid seal is provided between the particulate filter and the sides of the filter where the vortex and outlet chambers intersect so that the fluid must flow through the filter as it passes from the vortex chamber to the outlet chamber.

Particulates removed by the particulate filter accumulate on or near the filter medium and then often fall off the filter medium. These removed particulates fall downward where they accumulate in a meniscus shaped pile at the intersection between the bottom of the vortex chamber and the side of the particulate filter. The structure of the invention provides two such locations for these accumulations to occur, thus, decreasing the likelihood that the filter will become clogged with the removed particulates. One such location is on the exterior of the filter at the bottom of the vortex chamber, where it intersects with the outlet chamber. These particulates have been removed as the fluid flows into the filter. The second location is at the bottom of the filter itself where the fluid flows out through the filter medium into the outlet chamber.

The outlet chamber includes a valve seat and a check valve ball, or float, for terminating flow when the outlet chamber contains too much air or other gas. The density of the ball is such that it generally floats in the fluid but falls to the bottom to engage a valve seat when the outlet chamber contains excessive gas. Preferably, the diameter of the float is made large to reduce priming volume further, but this can result in the condition where the upward velocity of the ball is less than the downward velocity of the flowing fluid by entrainment of the ball in the fluid. To prevent this, the bottom of the filter is provided with several fairings that form a cage for receiving the ball and directing the fluid flow around the ball to shield it from the flow. This prevents entrainment of the ball in the downward fluid flow. Thus, during regular flow of the fluid, the ball floats and rises until it engages the bottom of the filter, and the check ball is maintained out of the fluid stream during normal operation of the device by the fairings.

As noted, the ball frequently becomes stuck against the seat and prevents further flow of fluid even after the gas has been evacuated and the outlet is again filled with fluid. Applicant has discovered that operation of a simple priming device creates a reverse flow of the fluid that forces the ball off the valve seat whereby it floats and allows fluid to pass. In the preferred embodiment, this device is a known pillow-type primer that is placed in the outline line just below the outlet chamber. Displacement of the check ball is effected by closing the outlet line below the pillow and squeezing the pillow to cause reverse flow of the fluid to displace the ball from the valve seat.

DETAILED DESCRIPTION OF THE PREFERRED EMBODIMENT

Figure 1:
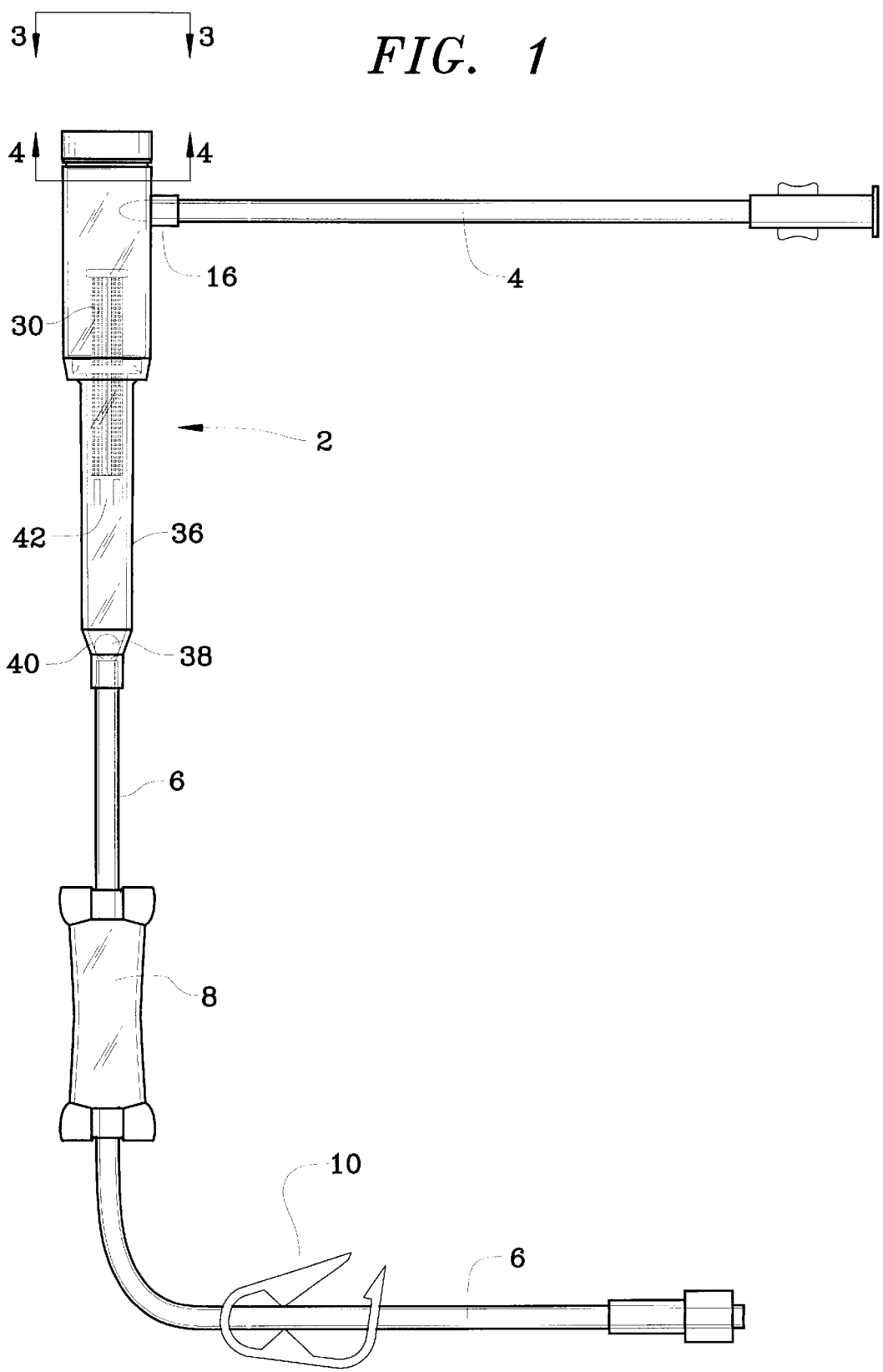
FIG. 1 is a side view of a filter system in accordance with the invention.

With reference to FIG. 1, a filter system in accordance with the invention includes a gas elimination filter 2, an inlet line 4, an outlet line 6, a pillow-type primer 8, and a tubing clamp 10. The inlet and outlet lines have Luer connectors, which are known in the art and allow the inlet line to be attached to a source of fluids and the outlet line to be attached to a patient line.

Figure 2:
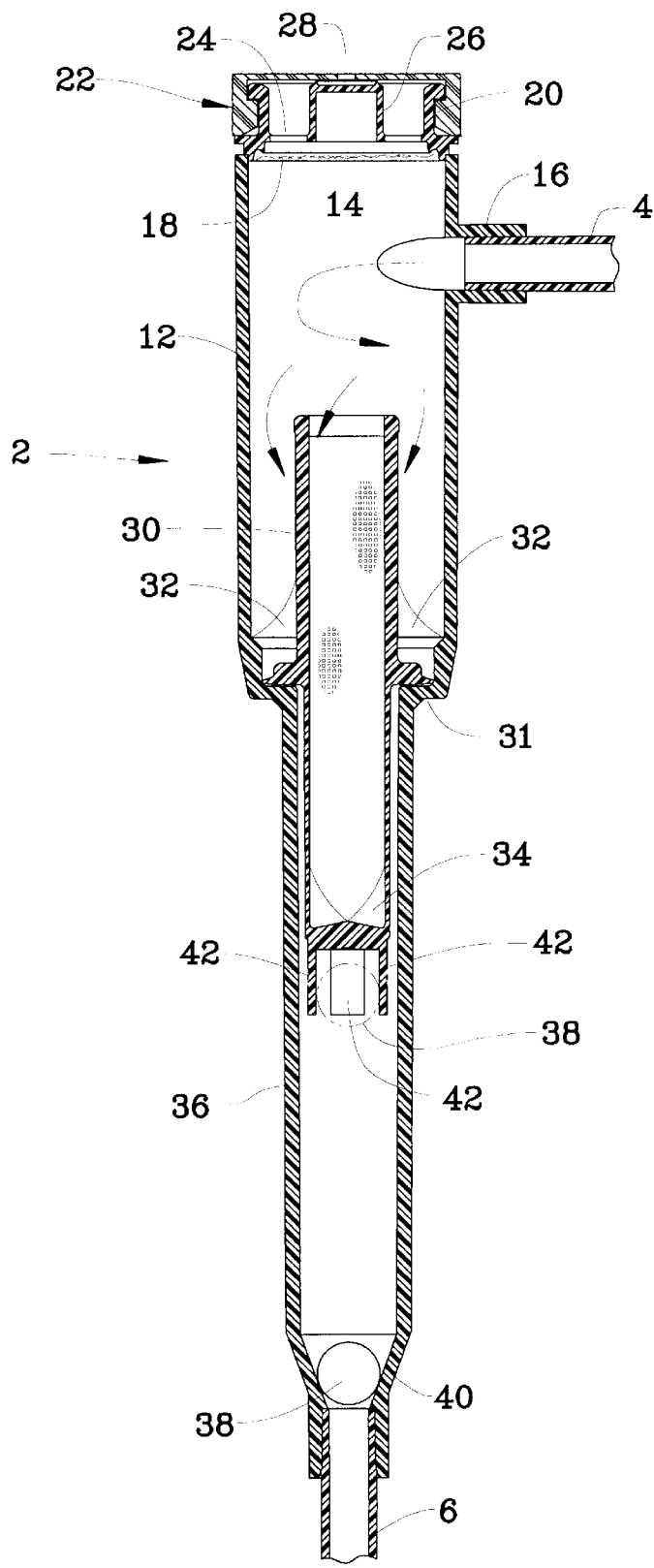
FIG. 2 is a vertical cross section of the filter of the system shown in FIG. 1.

FIG. 2 is a vertical cross section of the filter device and shows several features of the invention in more detail. An upper part 12 is generally cylindrical and forms a vortex chamber 14. While the vortex chamber is preferably cylindrical, it may be other shapes that support formation of a vortex in the inflowing fluid. An inlet port 16 directs the inflowing fluids into the chamber in a direction tangent to the outer wall of the chamber to form the vortex flow in the fluid. Because of density differences, gasses present in the inflowing fluids separate from the fluids and particulates by the forces in the vortex, the gasses generally accumulating in the central part of the vortex.

After separation, the gasses rise toward the top of the chamber and encounter a hydrophobic membrane 18, which covers the top of the chamber. The membrane 18 is held to the chamber by a cap formed of two parts. The membrane is attached, as by ultrasonic welding, to a first part 20, which is rigid and is sealed to the chamber during assembly. A second part 22 is flexible and snaps over the first part. The first part has holes 24, which allow passage of the gas that has passed through the membrane. After passage through the holes 24, the gas flows upward over a valve seat 26. The flexible cover 22 engages the valve seat 26, and an opening 28 in the cover is aligned with the valve seat. When the gas pressure in the area between the membrane and the flexible cover is greater than atmospheric, the gas will lift the cover from the valve seat, and the gas will exit the device through the hole 24. If, however, the gas pressure in the cap is lower than atmospheric, the cover will be pressed against the valve seat such that air cannot pass through the hole, thus preventing reverse flow of air into the device. In the preferred embodiment, the cover is biased slightly against the seat so that the pressure in the chamber must be greater that atmospheric by a predetermined amount before the cover will be lifted from the seat. This ensures that gas will not be drawn into the chamber when the pressure gradient is very small.

The fluid flowing into the vortex chamber is illustrated by arrows. The fluid forms a strong, descending vortex as it flows into the vortex chamber, and this vortex is allowed to exist for a substantial distance prior to encountering a particulate filter 30. The vortex chamber is preferably made of material that allows the operator to view this vortex during operation of the device to verify proper operation, such as a transparent plastic. As the fluid stream descends, it encounters the particulate filter 30. The particulate filter is open at the top whereby a portion of the fluid enters through the center of the particulate filter, and the remainder enters through the side wall of the filter. The vortex flow can continue in the fluid entering through the top, but the vortex action of the fluid is stopped in the main by interaction with the particulate filter.

In the preferred embodiment, the top of the particulate filter is below the center line of the inlet by about ⅝ to ¾ inch. The diameter of the particulate filter is about 40% of the diameter of the vortex chamber. Thus, in the embodiment shown, the inside diameter of the vortex chamber is about 0.940 inch, and the inside diameter of the particulate filter is about 0.360 inch. These dimensions have been found to allow adequate room for establishment of the vortex.

The particulate filter is preferably made of a material having about 170 $\mu$m mesh to provide superior filtration, and the described design allows this to be used without compromising the flow rate. The filter occupies parts of the vortex chamber and the outlet chamber. Preferably, the particulate filter is about evenly divided between these chambers, and the outside of the particulate filter is sealed to the outer wall of the vortex chamber by a flexible seal 31 to prevent movement of the fluid to the outlet chamber without first passing through the filter.

Particulates in the fluid in the vortex chamber flowing into the particulate filter through the side wall are removed and accumulate on the exterior of the filter. These particulates generally fall off the outer sides of the filter and accumulate at the bottom of the vortex chamber, as illustrated at 32.

Applicant has found that some of the gas not removed in the vortex flow will separate from the fluid as the fluid passes through the filter medium. This gas will either rise on the outside of the filter or accumulate on the side of the filter and eventually become detached. The gas in the fluid that passes through the particulate filter or enters through the top will separate from the fluid in the center of the particulate filter, and that gas will rise to the top of the chamber by passing through the open top of the filter.

The fluid flowing into the outlet chamber 36 through the particulate filter passes outwardly through the lower part of the filter medium as it flows into the outlet chamber. Thus, particulates remaining in the fluid that entered through the open top of the particulate filter are removed by passage through the lower part of the filter medium. These particulates accumulate on the interior of the filter and often fall off to accumulate in a pile on the bottom of the filter as illustrated at 34.

It will be appreciated that the above described construction provides a large filter area in a compact device while still allowing formation of a strong vortex in the incoming flow. Moreover, removal of particulates by passage through the two stage filter in both directions allows accumulation of removed particles in two separate locations, which increases the capacity of the filter for a given physical size.

The outlet chamber 36 is axially aligned with the vortex chamber and is generally of smaller diameter than the vortex chamber. This provides a smaller priming volume in the overall device while still providing adequate diameter for formation of a vortex in the vortex chamber. The outlet chamber also forms a check valve chamber for termination of flow when excess air is present. A spherical float 38 is located in the outlet chamber for performing the shut-off function. This float in preferably solid, to simplify sterilization and to provide a rigid-to-rigid contact with the valve seat to preclude wedging of the ball into the seat. The float may be made of a variety of materials and is preferably made of polypropylene.

The float operates in one of two positions. When the outlet chamber is full of air, the float is in the position shown in solid lines in FIG. 2 for termination of fluid flow. When the float is in the position shown in phantom lines, the outlet chamber is full of fluid as in normal operation, and the fluid is flowing freely.

The bottom of the outlet chamber forms a conical valve seat 40 for engaging the float 38 and terminating fluid flow. The sides of the taper preferably form an angle of about seventy degrees (70°) with the horizontal, which means that the angle between opposed sides of the seat form a forty degree (40°) angle. The angle between the opposing sides should be no less than thirty five degrees (35°). The float itself is sized such that the engagement between it and the seat occurs in a circle located about ⅝ths of the diameter of the float from the top of the float. These parameters have been found to provide a stable seal that is least likely to stick in the closed position.

The check valve of the present invention has been designed to provide a very efficient seal that operates effectively in the environment of flowing fluids. The angle of the valve seat is large to preclude wedging, the diameter of the ball is large to provide a stable seal, and there is virtually no deformation of the ball during contact between the rigid ball and the seat. These conditions, however, often result in contradictory requirements because a larger ball is more easily caught (entrained) in the downward fluid flow than a smaller ball, and a solid ball is generally less buoyant than a hollow one, which would deform during contact. Applicant's solution has been to provide a cage on the bottom of the filter, whereby, as the float rises to assume the position shown in phantom lines, the free-flowing position, it enters the cage formed by one or more fairings 42 that depend from the bottom of the particulate filter. In the preferred embodiment, there are four fairings. The bottom of the filter represents a stop to prevent further upward movement of the float, and the fairings hold the float centered in the outlet chamber so that it does not become entrained in the fluid flow. Thus, by guiding the flow of the fluid around the float, the fairings 42 provide an even flow at a higher flow rate without interference with the float and permit the ball to be larger.

With reference to the system shown in FIG. 1, the operation of the device is as follows. The inlet is attached to a source of physiological fluids for priming, and the clamp 10 is closed. This generally fills the filter device with fluid such that the float rises to the operational position. If the float is stuck, however, the operator will simply depress the pillow 8 one or more times. This action will force air in the outlet line 6 upward into the outlet chamber and dislodge the float from the valve seat. The fluid in the outlet chamber will then cause the float to rise to the operational position, and the air in the system will pass out through the membrane 18 as in normal operation. The clamp 10 can then be opened to fill the remainder of the line 6 with fluid.

The relationship between the size of the pillow and the size of the tube extending between the filter device and the pillow is important to whether air expelled from the pillow will be able to lift the float ball from the valve. If the tubing is too large, it will expand when the pillow is depressed, which will decrease the pressure applied to the ball, thus not providing adequate lifting of the float ball. Thus, the expansion capacity of the tube must be less than the volume of the pillow. In the preferred embodiment, the pillow has a volume of 12 cc, and the tube between the pillow and the check valve is about 1¾ inches long. The tube is 0.187 inside and 0.265" outside for higher flow rates or 0.130" inside and 0.190 outside for lower flow rates. It will be further appreciated that even though the pillow 8 is an inexpensive element, its positioning below the check valve greatly facilitates setup of the device.

Modifications within the scope of the appended claims will be apparent to those of skill in the art.

I claim:

1. A gas elimination filter comprising:
   a vortex chamber having an outer wall and an inlet in said outer wall oriented with respect to said outer wall such that a vortex is formed in said vortex chamber by fluid flowing in said inlet,
   a tubular particulate filter supported in said vortex chamber such that top of said particulate filter is spaced substantially below said inlet and said vortex is formed in the region between said inlet and said top of said particulate filter, and
   an outlet chamber having an outlet for said fluid and being in fluid communication with said vortex chamber, and wherein said particulate filter is open at its top, closed at its bottom and extends into said outlet chamber.

2. A gas elimination filter according to claim 1 wherein at least the portion of said chamber adjacent said region is transparent.

3. A gas elimination filter according to claim 1 wherein said chamber is cylindrical and said inlet admits said fluid to said chamber in a direction tangent to said chamber.

4. A gas elimination filter according to claim 1 wherein said vortex chamber and said outlet chamber are axially aligned.

5. A gas elimination filter according to claim 1 wherein said filter comprises a filter material in the form of a cylinder that is open at the top to said vortex chamber and closed at the bottom to said outlet chamber, some of said fluid in said vortex chamber passes to said outlet chamber by passing through said open top into the center of said particulate filter and then outwardly through said filter material into said outlet chamber and the remainder of said fluid passes from said vortex chamber inwardly through said filter material into the center of said particulate filter and then outwardly through said filter material to said outlet chamber.

6. A gas elimination filter according to claim 1 wherein said outlet chamber comprises a check valve.

7. A gas elimination filter according to claim 6 wherein said check valve comprises a valve seat formed in a wall of said outlet chamber and a float that engages said seat when said outlet chamber contains excess gas.

8. A gas elimination filter according to claim 7 further comprising a fairing on the bottom of said particulate filter arranged to receive said float when the outlet chamber is full of fluid.

9. A gas elimination filter according to claim 7 further comprising an outlet tube connected at one end to said outlet chamber downstream of said check valve and a primer connected to the opposed end of the outlet tube.

10. A gas elimination filter according to claim 9 wherein said primer is a compressible pillow primer.

11. A gas elimination filter comprising:
vortex chamber means for forming a vortex in a fluid stream for removal of gasses from said fluid,
outlet chamber means for receiving said fluid from said vortex chamber means, and
particulate filter means extending from said vortex chamber means into said outlet chamber means for removing particulates from said fluid stream.

12. A gas elimination filter according to claim 11 wherein said vortex chamber means includes a fluid inlet and said particulate filter is arranged in said vortex chamber such that said vortex forms in a region between said inlet and a top of said particulate filter.

13. A gas elimination filter according to claim 12 wherein said outlet chamber includes a check valve.

* * * * *